(12) United States Patent
Keller et al.

(10) Patent No.: US 10,244,946 B2
(45) Date of Patent: Apr. 2, 2019

(54) TEMPERATURE SENSOR, TEMPERATURE MEASURING DEVICE AND MEDICAL ENGINEERING SYSTEMS COMPRISING A TEMPERATURE SENSOR OR A TEMPERATURE MEASURING DEVICE

(71) Applicant: Aesculap AG, Tuttlingen (DE)

(72) Inventors: Anton Keller, Dürbheim (DE); Stefan Eick, Tuttlingen (DE); Thomas Maser, Zimmern ob Rottweil (DE); Christoph Rothweiler, Donaueschingen (DE); Sebastian Langen, Böhl-Iggelheim (DE); Raimund Hibst, Erbach (DE); Oliver Fugger, Ulm (DE); Detlef Russ, Renningen (DE)

(73) Assignee: Aesculap AG, Tuttlingen (DE)

( * ) Notice: Subject to any disclaimer, the term of this patent is extended or adjusted under 35 U.S.C. 154(b) by 969 days.

(21) Appl. No.: 14/345,486

(22) PCT Filed: Sep. 19, 2012

(86) PCT No.: PCT/EP2012/068401
§ 371 (c)(1),
(2) Date: Mar. 18, 2014

(87) PCT Pub. No.: WO2013/041550
PCT Pub. Date: Mar. 28, 2013

(65) Prior Publication Data
US 2015/0289767 A1    Oct. 15, 2015

(30) Foreign Application Priority Data
Sep. 19, 2011   (DE) .................. 10 2011 053 755

(51) Int. Cl.
*A61B 18/14*   (2006.01)
*A61B 5/01*    (2006.01)
(Continued)

(52) U.S. Cl.
CPC .............. *A61B 5/01* (2013.01); *A61B 5/6847* (2013.01); *A61B 5/6887* (2013.01); *A61B 5/742* (2013.01);
(Continued)

(58) Field of Classification Search
CPC .............. G01K 11/3213; G01K 13/002; A61B 18/1442; A61B 18/085;
(Continued)

(56) References Cited

U.S. PATENT DOCUMENTS 4,448,547 A * 5/1984 Wickersheim ............ G01J 5/48
                                                          250/337
4,626,110 A   12/1986 Wickersheim et al.
(Continued)

FOREIGN PATENT DOCUMENTS

CN   101495025    7/2009
DE   39 02 001 A1  7/1990
(Continued)

OTHER PUBLICATIONS

Chinese Office Action dated Sep. 6, 2015 in Chinese Application No. 201280048855.0, including English translation.
(Continued)

*Primary Examiner* — Thomas Giuliani
(74) *Attorney, Agent, or Firm* — RatnerPrestia

(57) ABSTRACT

In order to provide a temperature sensor or a temperature measuring apparatus having a temperature sensor, which enables direct temperature measurement, in particular even during treatment, in particular even with HF surgical devices, it is proposed that the temperature sensor includes a sensor element with a medium which can be excited to luminescence, in particular fluorescence, and an optical waveguide which is optically connected to the sensor element and is intended to supply light to the medium at an
(Continued)

excitation wavelength and/or to pick up and conduct light at a luminescence wavelength of the medium which can be excited to luminescence.

17 Claims, 7 Drawing Sheets

(51) Int. Cl.
    *A61B 18/18* (2006.01)
    *G01K 11/32* (2006.01)
    *G01K 13/00* (2006.01)
    *A61B 5/00* (2006.01)
    *A61B 18/20* (2006.01)
    *A61B 18/00* (2006.01)
    *A61B 17/00* (2006.01)

(52) U.S. Cl.
    CPC .......... *A61B 18/1442* (2013.01); *A61B 18/18* (2013.01); *A61B 18/20* (2013.01); *G01K 11/3213* (2013.01); *G01K 13/002* (2013.01); *A61B 2017/00101* (2013.01); *A61B 2018/0066* (2013.01); *A61B 2018/00589* (2013.01); *A61B 2018/00601* (2013.01); *A61B 2018/00619* (2013.01); *A61B 2018/00714* (2013.01); *A61B 2018/00797* (2013.01); *A61B 2018/00809* (2013.01); *A61B 2562/0271* (2013.01); *A61B 2562/0276* (2013.01)

(58) Field of Classification Search
    CPC .......... A61B 2018/00815; A61B 2018/00821; A61B 2018/00589; A61B 2018/00595; A61B 2018/00601; A61B 2018/00607; A61B 2018/0063; A61B 2018/00791; A61B 2018/00797; A61B 2018/00809; A61B 5/01; A61B 5/6847; A61B 2562/0271; A61B 2017/00101
    USPC ................. 600/549; 606/41, 50–52; 374/161
    See application file for complete search history.

(56) References Cited

U.S. PATENT DOCUMENTS

| | | | | |
|---|---|---|---|---|
| 4,925,327 A * | 5/1990 | Wirt | ................... | A61M 35/006 401/132 |
| 5,035,513 A | 7/1991 | Fehrenbach et al. | | |
| 5,304,809 A | 4/1994 | Wickersheim | | |
| 5,769,791 A * | 6/1998 | Benaron | ............... | A61B 5/0086 600/473 |
| 5,891,142 A * | 4/1999 | Eggers | ................ | A61B 18/1442 606/51 |
| 6,579,304 B1 * | 6/2003 | Hart | ........................ | A61B 17/02 606/157 |
| 2002/0183734 A1 | 12/2002 | Bommannan | | |
| 2002/0186748 A1 * | 12/2002 | Yates | .................. | G01K 11/3213 374/161 |
| 2005/0085806 A1 | 4/2005 | Auge, II et al. | | |
| 2007/0179484 A1 | 8/2007 | Sade | | |
| 2007/0191828 A1 | 8/2007 | Houser | | |
| 2008/0039836 A1 | 2/2008 | Odom | | |
| 2008/0125767 A1 | 5/2008 | Blaha | | |
| 2009/0054908 A1 | 2/2009 | Zand | | |
| 2009/0261804 A1 * | 10/2009 | McKenna | ........... | A61B 18/1442 324/71.1 |
| 2011/0015632 A1 * | 1/2011 | Artale | ................. | A61B 18/1445 606/51 |
| 2011/0092972 A1 * | 4/2011 | Allen | ............. | A61B 17/320092 606/45 |
| 2011/0270252 A1 * | 11/2011 | Horner | ................ | A61B 18/1445 606/52 |

FOREIGN PATENT DOCUMENTS

| | | |
|---|---|---|
| DE | 60206742 T2 | 4/2006 |
| EP | 1244390 | 8/2006 |
| JP | 2002340698 | 11/2002 |
| JP | 2003093402 | 4/2003 |
| JP | 2007229454 | 9/2007 |
| WO | WO 03/012468 A1 | 2/2003 |
| WO | WO 2009/005850 A1 | 1/2009 |

OTHER PUBLICATIONS

German Search Report for related German Application No. 10 2011 053 755.4, dated May 25, 2012.
Second Chinese Office Action dated Apr. 20, 2016 for Chinese Application No. 201280048855.0, including English translation, 17 pages.
International Search Report issued in related International Application No. PCT/EP2012/068401, dated Jul. 29, 2013.
Japanese Office Action dated Jun. 21, 2016 for Japanese Application No. 2014-530276, including English translation, 8 pages.

* cited by examiner

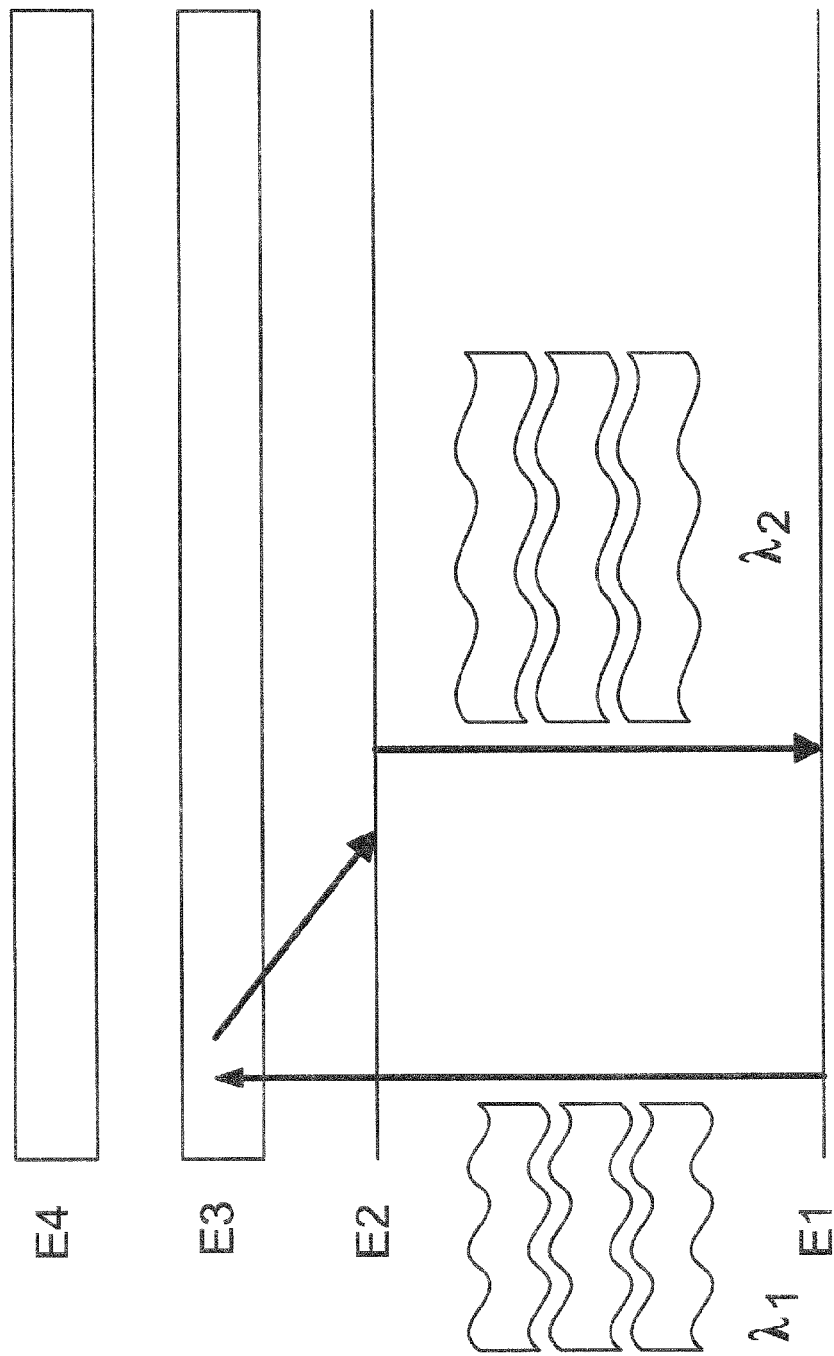

TEMPERATURE SENSOR, TEMPERATURE MEASURING DEVICE AND MEDICAL ENGINEERING SYSTEMS COMPRISING A TEMPERATURE SENSOR OR A TEMPERATURE MEASURING DEVICE

RELATED APPLICATIONS

This application is the U.S. National Phase of International Application No. PCT/EP2012/068401, filed Sep. 19, 2012, which claims the benefit of priority of German Application No. 10 2011 053 755.4, filed Sep. 19, 2011, the contents of both applications being incorporated by reference herein and for all purposes.

FIELD

The invention relates to temperature sensors for medical engineering systems, temperature measuring devices containing such temperature sensors as well as to those medical engineering systems which comprise said temperature sensors or temperature measuring devices.

BACKGROUND

The measurement of temperature in medical treatments and therapies, in particular also in surgery, is of importance in many ways, in particular for determining a progress in the therapy or treatment, to control it and, as the case may be, finish it.

With conventional temperature sensors, an uninfluenced measurement of temperature parallel to ongoing therapies or treatment measures, in particular also surgical interventions, is not possible in many cases, as there is a multitude of environmental factors which affect the measurement of temperature and thus falsify the temperature value actually to be determined.

To give an example, both electric disturbances in surgical RF devices and the direct warming up of the sensors when heated by a laser beam play an important role as disturbing factors. In electrosurgical interventions, a control of the process is accomplished at present by measuring the electric impedance of the treated tissue structure, correlating with the water content of the tissue structure. During the supply of RF current, however, the measurement of temperature cannot be performed.

Also in the case of applying lasers, a direct measurement of temperature by means of thermocouples or thermistors is not possible due to the inherent absorption of laser energy by these elements.

The above-mentioned measurement of the impedance is capable of reflecting the reaction of the tissue structure to the thermal stimulus only as an indirect quantity. A substantial change in the impedance, however, only occurs if a considerable amount of the tissue water is evaporated. Indeed, the tissue structure itself is affected and altered already at significantly lower temperatures. By way of example, conformation modifications in the collagen are already reached at temperatures of approximately 70° C. Apart from the temperature, also the exposure time of the temperature stimulus plays an important role. Such processes as well as other chemical reactions are described by the Arrhenius coefficient.

Further, the measurement of impedance is highly dependent on the size of the area of the tissue structure relevant in the measuring process as well as on the distance and contact pressure of the electrodes.

Furthermore, document WO 2009/005850 A1 discloses to use the measurement of the light transmission for evaluating the state of the treated tissue. This measurement process is prone to malfunctions with respect to soiling and in many cases is not sufficiently meaningful regarding the state reached by the observed tissue.

SUMMARY

It is the object of the present invention to propose a temperature sensor or a temperature measuring device which allows for a direct measurement of temperature, in particular also during the treatment, in particular also with surgical RF devices.

This object is achieved according to the invention by a temperature sensor and a temperature measuring device comprising such a sensor.

The present invention exploits the effect that the quantum yield, preferably the luminescence quantum yield, in particular also the fluorescence quantum yield, depends on temperature and hence is a measure for the temperature of a sensor element which may be excited to show luminescence.

The determination of the temperature of a sample on the basis of the temperature dependency of the fluorescence quantum yield of fluorescent media is known per se from WO 03/012468 A1. This document proposes to apply a fluorescent medium to the surface of electronic components whose temperature is affected by modulated electric energy. The fluorescence which is irradiated by the sample surface which has been exposed to excitation light and modified in this way, is received by an image capture device and evaluated in the state of being coupled to the phase of the modulation frequency of the electric energy.

Unlike this conventional method, the present invention acts—with regard to the luminescent medium and the light capture element in the form of a light conductor—with a closed system in the sense that the observation of the luminescence quantum yield is accomplished so as to be unaffected by other environmental influences and hence can be successfully employed in many medical engineering systems for the first time.

For the purpose of precisely determining the temperature of the observed sample, the present invention does not need any expensive measuring equipment and allows in particular for the measurement of temperature on sample surfaces which are typically not accessible to an optical observation.

As the temperature sensor according to the invention is optically coupled to a light conductor delivering the light to the luminescent medium and discharging the luminescence of the medium, independently of the optical circumstances of the environment of the temperature sensor, any soiling of the sensor element in an operation environment does not affect the measuring result.

In the context of the determination of the luminescence quantum yield, the temperature measuring process used according to the invention is also insensitive to electric disturbances which may occur for example during use of surgical RF devices. Even a parallel use of laser light in the course of a therapeutic treatment will not cause any disturbance, because the light frequencies for the laser treatment, on the one hand, and the excitation wavelength as well as the luminescence wavelength of the sensor element, on the other hand, can be selected in each case such that there is no impact on the measurement of the luminescence quantum yield.

Further, the size of the sensor element comprising the medium showing luminescence upon excitation can be kept very small, so that the heat capacity of the sensor element is negligible as such and current temperature changes of the surrounding tissue structure can be monitored via the measurement of the luminescence.

With the aid of the direct measurement of temperature which is possible according to the invention, the state of the tissue can be characterized already during the application of high-frequency current or laser light and a desired sealing process of tissue structures can be checked. The calculation of the state of the tissue can then be accomplished via the above-mentioned Arrhenius coefficient.

The temperature sensors and temperature measuring devices according to the invention can be used for high-frequency applications as well as for laser applications or any other forms of energy for heating tissue structures. Measuring the temperature with the temperature sensors according to the invention (or temperature measuring devices equipped with such sensors) does further not depend on the size of the treated tissue structure and the electrode spacing.

Preferred temperature sensors of the invention comprise a common light conductor for delivering light with the excitation wavelength, on the one hand, and for receiving and discharging light having the luminescence wavelength, on the other hand. It is further preferred that the sensor element is directly connected to the light conductor(s).

The sensor elements for the temperature sensors according to the invention may comprise the medium showing luminescence upon excitation in a sleeve which surrounds the medium and may be designed in particular so as to be rigid. The sleeve may be designed so as to be optically transmissible or opaque, for instance reflecting towards the inside.

The medium showing luminescence upon excitation may be a medium capable of flowing, in particular a gel.

Preferably preferred media showing luminescence upon excitation are media in the form of solid bodies, in particular crystals which are used in solid state lasers. These include ruby, sapphire, doped yttrium aluminum garnet (YAG) crystals, for instance ER:YAG, ND:YAG, YB:YAG as well as alexandrite.

Particular advantages of these materials are their high thermal conductivity, resistance to temperature and mechanical strength.

On the other hand, solids in the form of plastic materials such as PEEK functionalized with fluorescence dyes may be used as media showing luminescence upon excitation. The advantages of the functionalized plastic materials are their varied availability, simple processability as well as the low cost of materials. In particular PEEK is distinguished by an extensive use in medical technology and the good resistance to temperature.

Further, other temperature-resistant plastic materials functionalized with fluorescence dyes are also suitable, for instance epoxy resins.

In the case of plastic materials functionalized with fluorescence dyes, the plastic material can be selected from a high number of available materials which can moreover be adapted to the respective application.

If the temperature sensors according to the invention are equipped with a rigid sleeve surrounding the fluorescent medium or designed as a solid body as described, the temperature sensors themselves may serve as spacers with RF applications, keeping the electrodes at a defined spacing in order to prevent a short-circuit when the electrodes are supplied with electric current.

Having such a dual use as a temperature sensor and as a spacer, the measurement of temperature is simultaneously performed as close as possible to the spot of energy input, i.e. in direct contact with the treated volume of the tissue structure. The spacers and the sensor elements immediately allow for the observation of the temperature change in the vicinity.

Apart from the temperature sensors which have already been described in detail, the temperature devices according to the invention for medical engineering systems additionally comprise a light source irradiating the excitation wavelength, in particular a laser, as well as a luminescence detector such as a photo cell.

Preferred temperature measuring devices comprise several temperature sensors which are received and arranged in the form of a two- or three-dimensional matrix in a mount with predefined distances between one another. Owing to the possible small dimensions of the sensor elements of the temperature sensors according to the invention, they can be integrated in many conventional components of surgical instruments and medical engineering systems, with the option that the components serve as a mount.

Finally, the invention relates to medical engineering systems comprising one or more of the temperature sensors according to the invention or a temperature measuring device as described above.

Preferred medical engineering systems are implemented as surgical systems, in particular as ultrasound, laser or electrosurgical systems.

Preferred medical engineering systems of the present invention are distinguished in that the surgical system comprises a device for cutting, dissection, coagulation, sealing and/or connection of tissue structures of a patient.

Due to employing the temperature sensors according to the invention, it is possible here to detect the change in the tissue structures much more precisely and at an earlier point in time as is the case with the conventional measurement of impedance, as the water content of the treated tissue structure does not have a direct impact on the measurement of temperature.

As the temperature sensors according to the invention, with the appropriate selection of the sensor elements of materials which are highly resistant to mechanical stress and elevated temperatures, can be directly applied to the treated tissue structure, a direct measurement of temperature is achieved here, which is far superior to the measurement of infrared radiation emanating from a treated tissue structure and recommended in the prior art as an alternative. Reference can be made in this respect to US 2007/0179484 A1, for example.

In many cases, medical engineering systems according to the invention for the treatment of tissue structures comprise an applicator tool having two applicator elements, in particular in the form of so-called applicator jaws which can be moved relative to each other and transferred from an open rest position to a closed working position. Here, one of the temperature sensors according to the invention will be arranged preferably in at least one of the applicator elements or at least one of the applicator jaws.

The applicator elements, in particular if they are part of a surgical RF device, comprise a spacer which keeps the applicator elements in the working position a predefined distance apart from each other, the spacer comprising in particular a temperature sensor of the present invention. It is in particular possible that the temperature sensor or its sensor element itself is/are implemented as a spacer.

Preferred medical engineering systems of the present invention comprise a protective mechanism which blocks the activation of the temperature sensor(s) unless the applicator elements are in a predefined application position, in particular in the working position. This measure prevents the temperature sensors of the medical engineering system from irradiating light into the surroundings by accident. This is of particular importance if a laser is used as the light source for the excitation of luminescence.

The above-mentioned protective mechanism preferably comprises a switching element, in particular an optical, electrical or mechanical contact maker monitoring the position of the applicator elements.

The protective mechanism may further comprise a separate temperature sensor for measuring the temperature of at least one of the applicator elements, so that this temperature sensor makes it possible to check if the applicator elements already have contact with a tissue structure which typically is at body temperature.

As already mentioned, the medical engineering systems according to the invention are preferably equipped with an RF generator, a temperature measuring device or sensor according to the invention, a device for evaluating a temperature profile and/or a device for regulating or controlling a system-related function depending on the temperature value measured by the temperature sensor.

In further preferred medical engineering systems of the present invention, the applicator elements are equipped with a structured surface area which facilitates the gripping of the tissue structure in an especially reliable manner. This measure avoids in particular any inadvertent shifting movement of the tissue to be treated relative to the applicator elements during the therapeutic treatment.

Surfaces structured in the manner of a grid are particularly suitable as structured surfaces.

Further preferred medical engineering systems also comprise a metering device for a primer material, with the option that this primer material can be made available in particular in the form of a material based on collagen or gelatin.

BRIEF DESCRIPTION OF THE DRAWING FIGURES

These and other advantages of the invention will be explained in more detail with the aid of the drawings in which:

FIG. 3 is a schematic illustration of the functional principle of the temperature sensor according to the invention;

DETAILED DESCRIPTION

Figure 1:
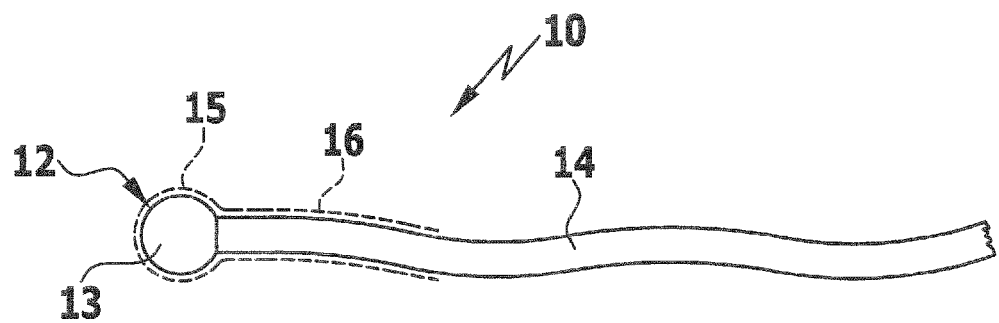
FIG. 1 shows a temperature sensor of the present invention.

FIG. 1 shows a temperature sensor of the present invention which on the whole is provided with the reference symbol 10 and comprises a sensor element 12 in the form of a ball-shaped ruby crystal and a light conductor 14 attached thereto which is optically connected to the sensor element 12. In this embodiment of the temperature sensor 10 according to the invention, only a single light conductor 14 is provided, serving both for supplying light with the excitation wavelength for the luminescence of the excitable medium 13 of the sensor element 12 and for receiving and discharging the luminescence which is emitted from the medium 13 and induced by the excitation wavelength. The sensor element 12 may comprise a sleeve 15 (shown in dashed lines in FIG. 1) which surrounds the medium 13 and connects the sensor element to the light conductor 14. Optionally, the light conductor 14 may be surrounded by a cladding material 16 (shown in dashed lines in FIG. 1) which for its part is connected to the sleeve 15 of the sensor element preferably in a substance-to-substance bond.

Figure 2A:
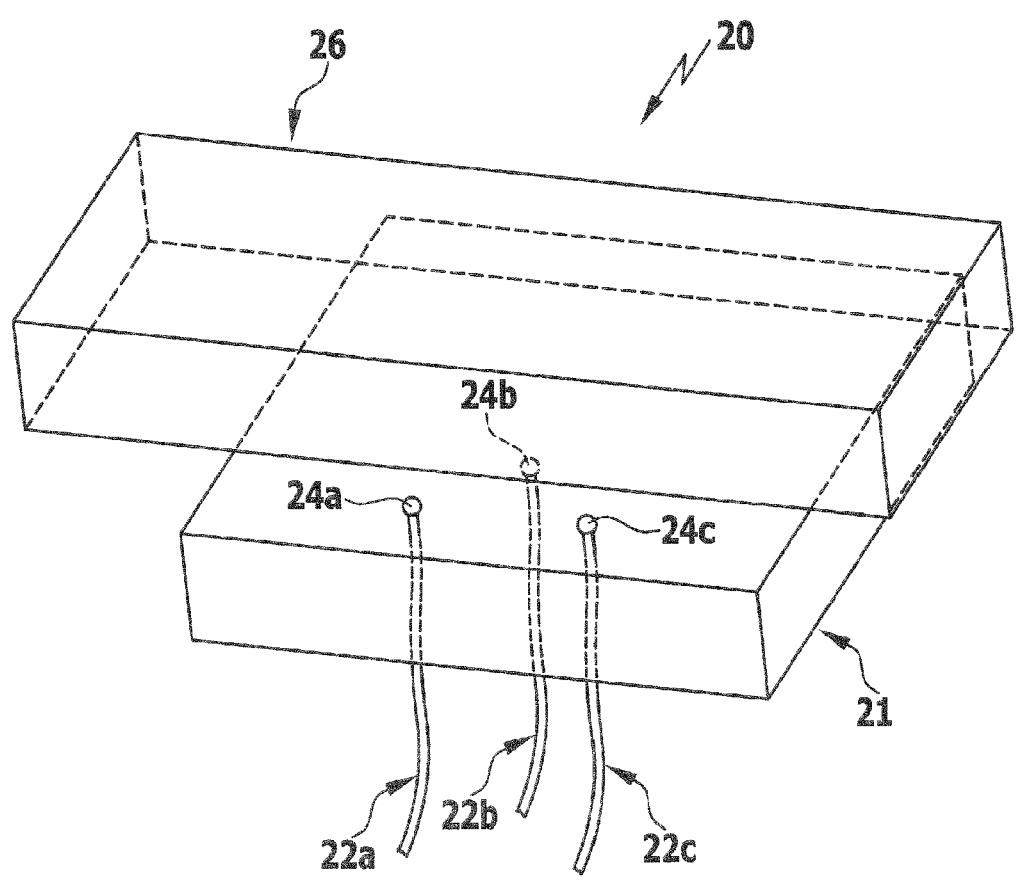
FIGS. 2A and 2B show the temperature sensor of FIG. 1 in two different sensor arrangements.

FIG. 2A shows a temperature measuring device 20 in which three temperature sensors 22a, 22b and 22c are supported in a mount 21 such that their sensor elements 24a, 24b and 24c are arranged in a triangular matrix.

The sample body 26 shown schematically offers the opportunity to determine the temperature in a spatially resolved manner.

Figure 2B:
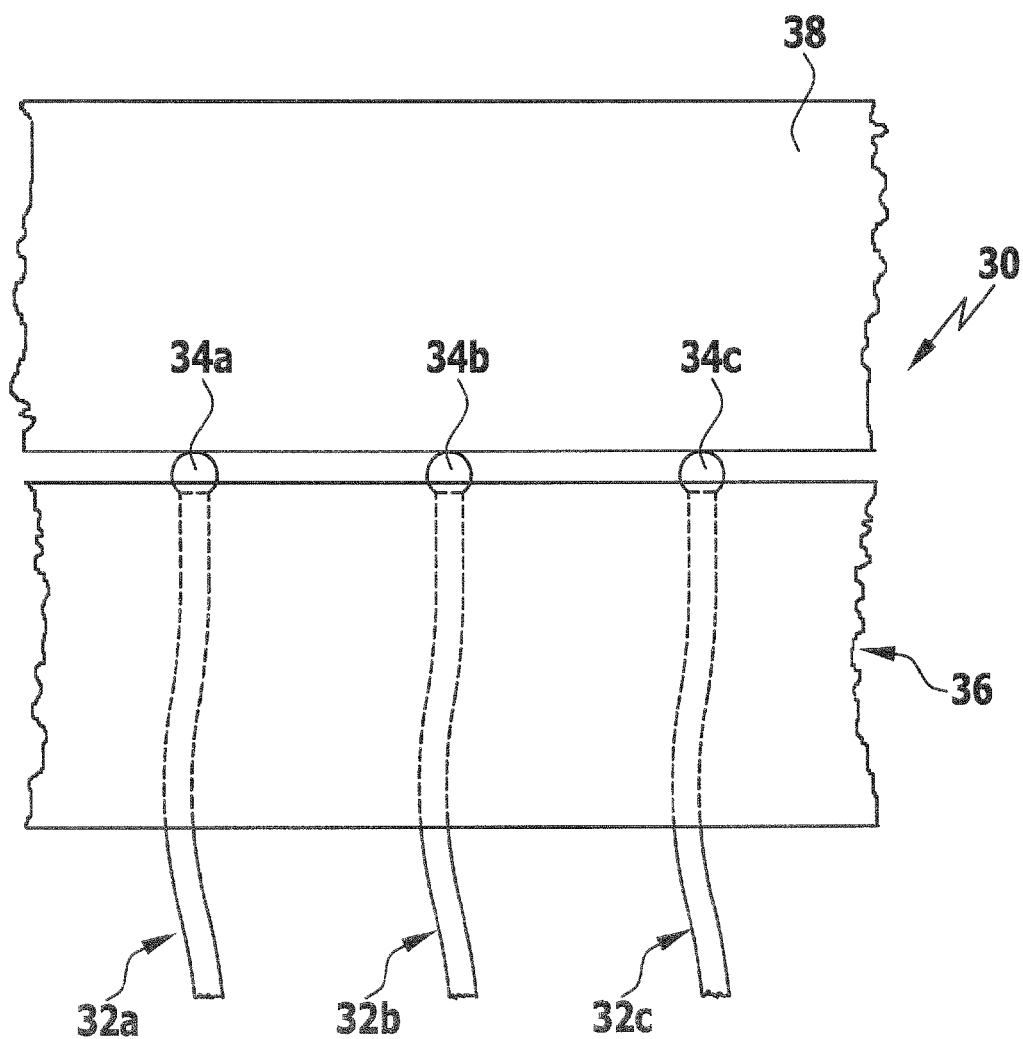

FIG. 2B shows a temperature measuring device 30 which also comprises three temperature sensors 32a, 32b, 32c kept spaced from each other such that their sensor elements 34a, 34b and 34c are linearly arranged at equal intervals.

At the same time, the sensor elements 34a, 34b, 34c protrude from the surface of the mount 36 and in this way define a distance to a body 38 which, in combination with the mount 36, may constitute a pair of applicator elements for instance for high-frequency current.

FIG. 3 schematically shows the functional principle of the luminescent media of the sensor elements of the temperature sensors according to the invention.

By means of absorption of the light having an excitation wavelength $\lambda 1$, the medium showing luminescence upon excitation changes from an energetic state E1 to an energetically excited state E3, from which the medium goes back to the excited state E2 thermally by relaxation. Under the emission of light with the wavelength $\lambda 2$, the system returns from the excited state E2 to the energetic state E1. This shall be described in more detail below on the basis of a ruby crystal representing a medium showing luminescence upon excitation.

In ruby crystals, chromium ions are responsible for luminescence which is irradiated here in the form of fluorescence. The chromium ions possess optimum spectral absorption bands via which fluorescence light can be excited with large quantum yield. One of the absorption bands in the green spectral range allows for an excitation of the ruby crystal (as the medium showing luminescence upon excitation) with an excitation wavelength $\lambda 1$ of approximately 532 nm, whereas the emission wavelength $\lambda 2$ in the red spectral range is approximately 694 nm. The observed quantum yield depends on temperature, i.e. the ratio of the number of emitted photons to absorbed photons decreases with rising temperatures. This temperature dependency is sufficiently pronounced in the temperature range between approximately 30 and approximately 150° C. which is of interest for medical science, in order to provide sufficiently exact temperature values of treated tissue structures.

The two wavelengths of the excitation light and the fluorescence light are spaced from each other so far that their light proportions can be optically separated without any problems and the quantum yield of the fluorescence having the wavelength $\lambda 2$ can be determined in an easy and accurate manner.

Figure 4:
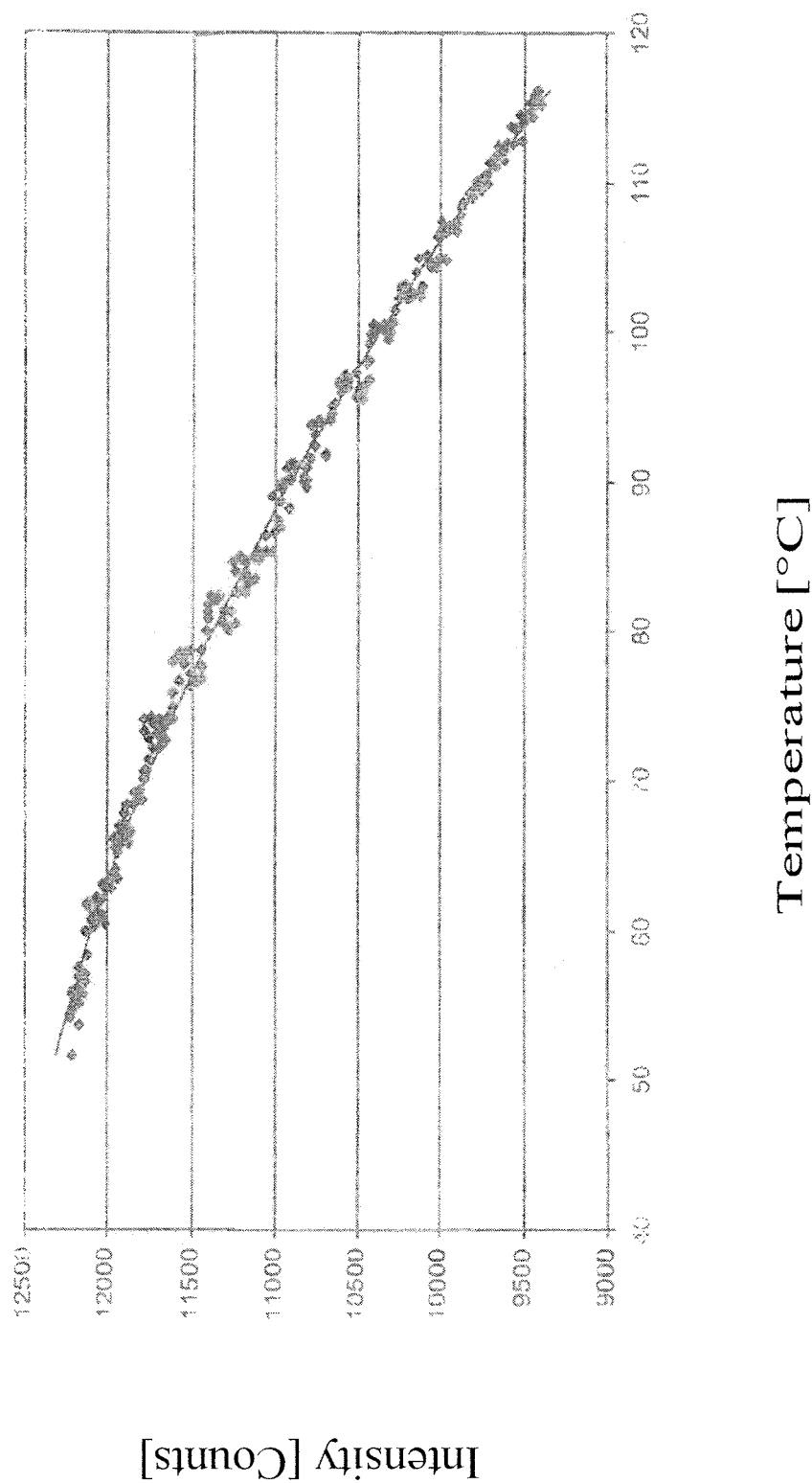
FIG. 4 shows the temperature independency of the fluorescence quantum yield of a temperature sensor according to the invention.

FIG. 4 shows the fluorescence quantum yield of a ruby crystal versus temperature in the range from 50 to 115°, and the resultant curve may serve for the calibration of a temperature sensor according to the invention comprising a ruby crystal, which is used for sealing tissue structures.

It can be seen that there is an almost linear dependency between the temperature, on the one hand, and the fluorescence quantum yield (here plotted as the intensity or the counts of a photo diode). The measured values were obtained at a constant excitation light intensity with a ruby crystal placed in a temperature-controlled furnace.

Figure 5:
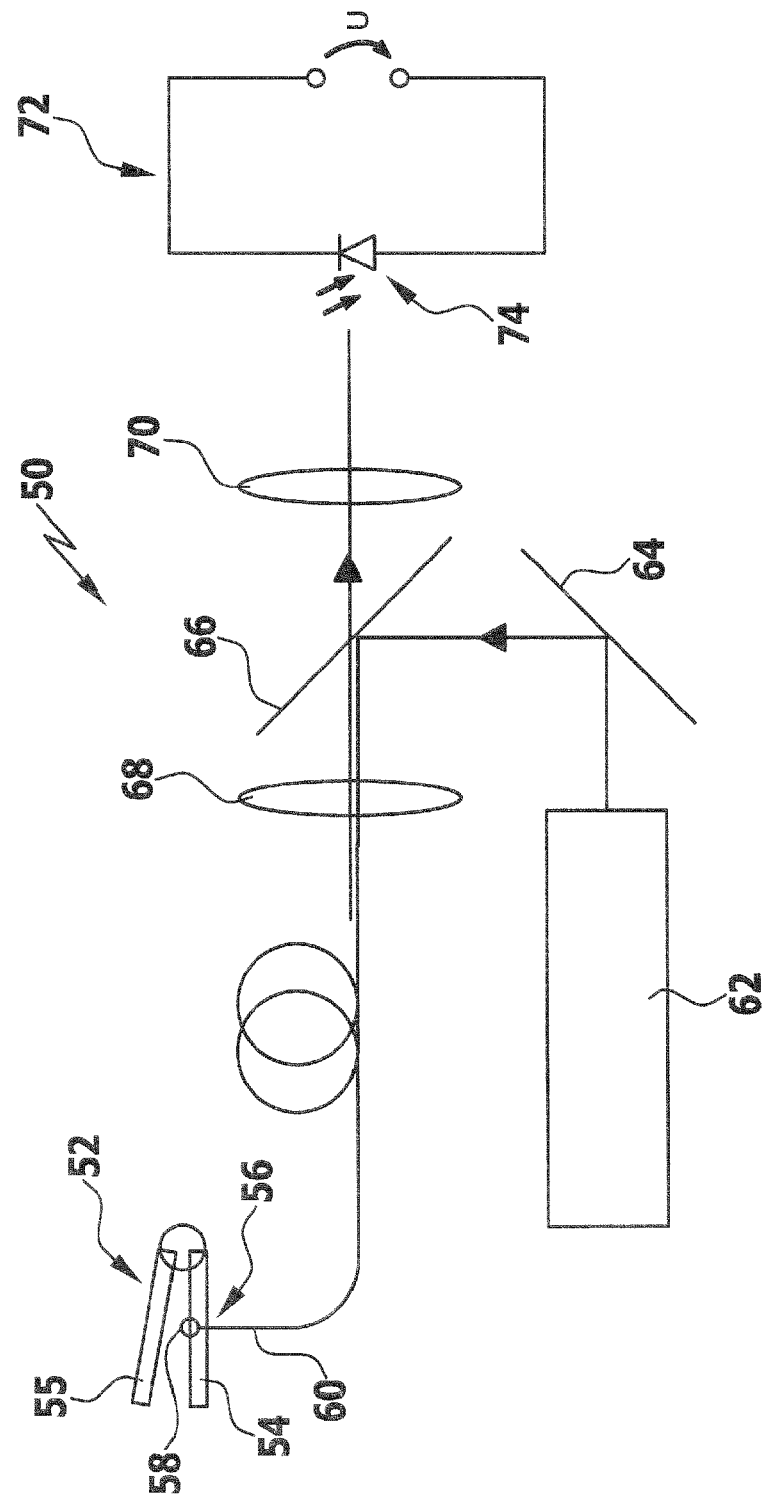
FIG. 5 shows a medical engineering system of the present invention.

FIG. 5 shows a schematic illustration of a medical engineering system 50 according to the invention.

The medical engineering system 50 comprises a device (provided with the reference symbol 52) for sealing and/or connecting tissue structures of a patient. In the schematic illustration of FIG. 5, this device is illustrated so as to be reduced to two applicator jaws 54, 55 which are pivotally connected with each other. The generator required for supplying electric current to the applicator jaws 54, 55 as well as the device for applying the applicator jaws 54, 55 to a tissue structure are known to a person skilled in the art and are omitted in FIG. 5 for simplicity.

A temperature sensor 56 according to the invention is arranged in one of the applicator jaws 54, whose sensor elements 58 are designed in such a manner and arranged in the applicator jaws 54 such that it is able to also take over the function of a spacer preventing the two applicator jaws 54 and 55 from directly coming into an electrically conductive contact, avoiding in this way a short-circuit between the two jaws 54 and 55.

Apart from the sensor element 58, the temperature sensor 56 comprises a light conductor 60 attached thereto.

The medical engineering system 50 further comprises a light source in the form of a laser 62 whose laser beam is coupled into the light conductor 60 via a mirror 64 and a dichroic mirror 66. The laser 62 is a Nd:YAG laser whose output light is doubled in frequency and thus has a wavelength of approximately 532 nm.

The optical system used for coupling is schematically represented in FIG. 5 by a lens 68. Via the light conductor 60, the excitation light of the laser 62 is radiated into the sensor element 58 and the medium showing luminescence upon excitation arranged therein (in the present example again a ruby crystal) and generates here the fluorescence with a wavelength of approximately 694 nm, as described above in the connection with FIGS. 3 and 4, which is emitted by the ruby crystal in isotropic fashion. The light conductor 60 detects in fact only a fraction of this emitted radiation, but detects said fraction in a constant manner, so that the fluorescence light of the ruby crystal of the sensor element 58 received by the light conductor 60 is representative for the total quantum yield. The fluorescence light is transmitted by the light conductor 60 through the optical system 68 and penetrates the dichroic mirror 66 which has such a design that it reflects the excitation wavelength of approximately 532 nm whereas it permits the wavelength of 694 nm to pass. Having passed the dichroic mirror 66, the red fluorescence light is guided via a further optical system 70 to a detector 72 and its photodiode 74, with the voltage signal U which is generated here being evaluated as intensity.

The temperature sensor 56 in combination with the sensor element 58 and the light conductor 60 as well as the laser 62 as the light source and the detector 72 constitute a temperature measuring device of the present invention. In preferred embodiments of the temperature measuring device according to the invention, as illustrated in FIG. 5 as part of the medical engineering system 50, the light conductor 60 serves both to transport the light with the excitation wavelength to the sensor element 58 and to transport the luminescence of the excited medium to the detector 72. The optical systems 68 and 70 as well as the mirrors 64 and 66 provide for optimized light paths within the temperature measuring device.

Due to the fact that the sensor element 58 and the ruby crystal which is used as the medium showing luminescence upon excitation are arranged so as to protrude from the surface of the applicator jaw 54, it is in direct contact with the tissue situated between the applicator jaws 54, 55, so that any temperature change of said tissue is directly transferred to the sensor element 58. Due to the temperature dependency of the quantum yield of the fluorescence of the ruby crystal (cf. FIG. 4), the temperature of the tissue which is held between the two applicator jaws 54, 55 can be determined from the different voltage signals of the detector 72.

Figure 6:
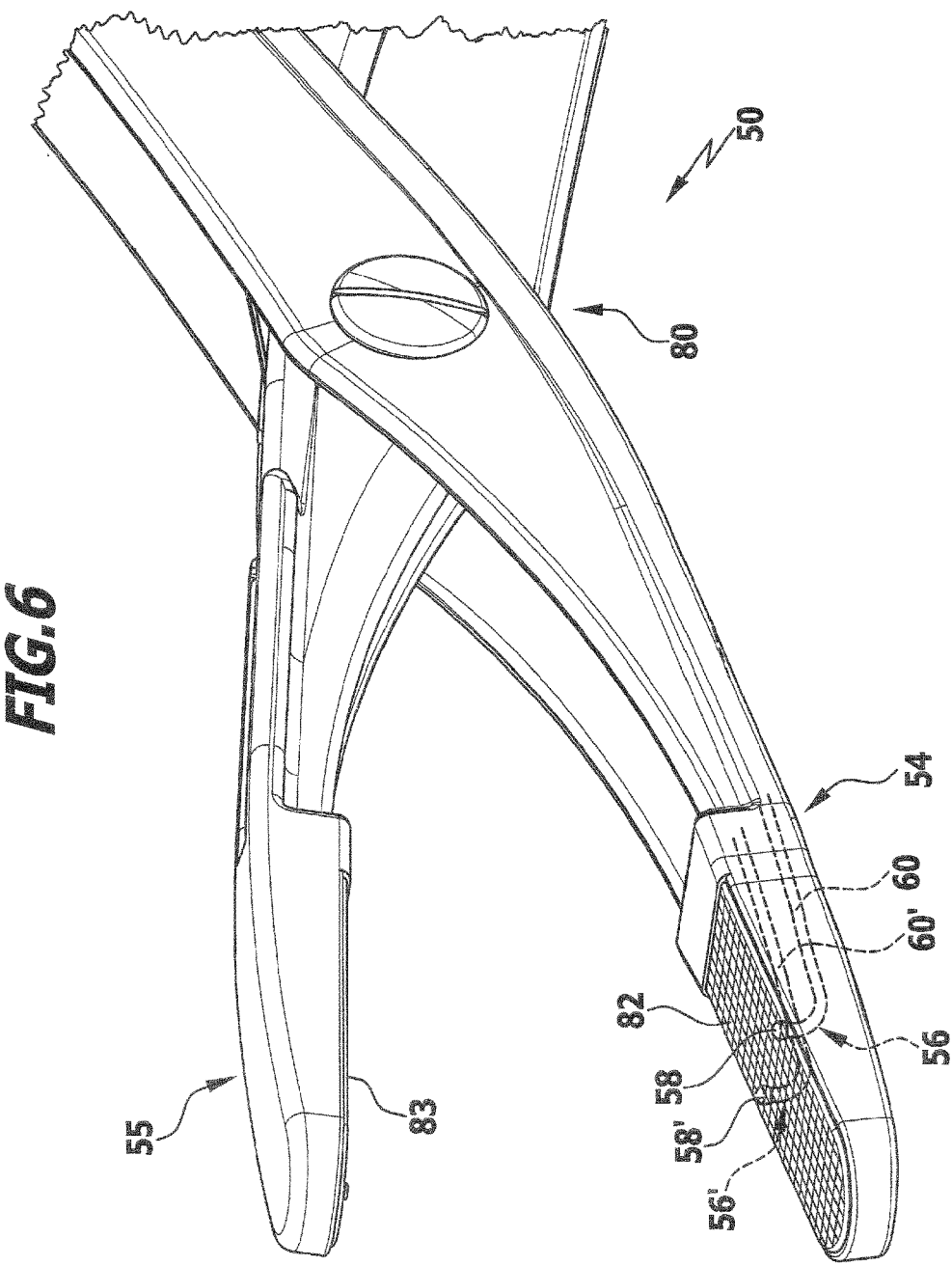
FIG. 6 shows a part of the medical engineering system of FIG. 5 in an enlarged and detailed illustration.

FIG. 6 shows by way of example the two applicator jaws 54, 55 in detail again, which are pivotally supported by means of a hinge portion 80 so as to be electrically isolated from each other.

Two temperature sensors 56, 56' are arranged with their sensor elements 58, 58' in the applicator jaws 54, with the sensor elements 58, 58' comprising their medium showing luminescence upon excitation projecting from the surface of the applicator jaw 54 and in this way forming a stop, i.e. a spacer for the closing position of the applicator jaw 55. The two applicator jaws 54, 55 are equipped with electrically conductive electrodes 82, 83 which can be supplied with electric current and preferably comprise, as is shown in FIG. 6, a structured surface, in particular a surface which is structured in the manner of a grid and prevents the tissue material to be treated, which is held between the applicator jaws 54, 55, from slipping during the treatment.

The invention claimed is:

1. A medical engineering system comprising at least one temperature sensor comprising a sensor element including a medium showing luminescence upon excitation, the medium showing luminescence upon excitation being a crystal, the at least one temperature sensor also comprising a light conductor which is optically connected to the sensor element and is intended for supplying the crystal with light having an excitation wavelength and/or for receiving and discharging light having a luminescence wavelength of the crystal, the medical engineering system being implemented as a surgical system, wherein the surgical system comprises a device for cutting, dissection, coagulation, sealing and/or connecting tissue structures of a patient, the device comprising an applicator tool with two applicator elements in the form of applicator jaws which can be moved relative to each other and can be transferred from an open resting position to a closed working position, the at least one temperature sensor being arranged in at least one of the applicator elements, said at least one of the applicator elements comprising at least one spacer which keeps the applicator elements in the working position at a predefined distance relative to each other, the at least one spacer forming the at least one temperature sensor, wherein the applicator jaws each extend in a longitudinal direction, and wherein the light conductor of the at least one temperature sensor extends inside one of the applicator jaws in the longitudinal direction.

2. The medical engineering system according to claim 1, wherein the medical engineering system comprises a protective mechanism which blocks the activation of the at least one temperature sensor unless the applicator elements are in the working position.

3. The medical engineering system according to claim 2, wherein the protective mechanism comprises an optical, electrical or mechanical contact maker monitoring the position of the applicator elements.

4. The medical engineering system according to claim 2, wherein the protective mechanism comprises a separate temperature sensor for determining the temperature of at least one of the applicator elements.

5. The medical engineering system according to claim 1, wherein the medical engineering system comprises an RF generator, a temperature measuring device, a device for evaluating a temperature profile and/or a device for regulating or controlling a system-related function depending on temperature values measured by the at least one temperature sensor.

6. The medical engineering system according to claim 1, wherein the applicator elements comprise a structured surface area which facilitates the gripping of tissue structures.

7. The medical engineering system according to claim 6, wherein the structured surface area comprises a grid-like surface structure.

8. The medical engineering system according to claim 1, wherein the medical engineering system comprises a metering device for a primer material based on collagen or gelatin.

9. The medical engineering system according to claim 1, wherein the luminescence wavelength of a discharged light signal of the at least one temperature sensor is adapted to form the basis of a quantum yield observation to which a specific temperature is associated in each case.

10. The medical engineering system according to claim 1, wherein the conductor is a common light conductor for supplying, receiving and discharging light having the excitation wavelength and the luminescence wavelength.

11. The medical engineering system according to claim 1, wherein the sensor element is directly connected to the light conductor.

12. The medical engineering system according to claim 1, wherein the sensor element comprises the medium showing luminescence upon excitation in a sleeve which surrounds the medium and is designed so as to be rigid.

13. The medical engineering system according to claim 1, comprising a laser and a luminescence detector in the form of a photo cell.

14. The medical engineering system according to claim 1, wherein the at least one temperature sensor comprises a plurality of temperature sensors in the form of a two- or three-dimensional matrix received in a mount, the plurality of temperature sensors having predefined distances relative to one another.

15. The medical engineering system according to claim 1, wherein the crystal is a ruby.

16. The medical engineering system according to claim 1, wherein the crystal is a sapphire or a body containing YAG materials.

17. The medical engineering system according to claim 1, wherein the applicator jaws each comprise a structured surface, and wherein the sensor element of the at least one temperature sensor projects from the structured surface to form said at least one spacer.

* * * * *